United States Patent
Orlowski et al.

(10) Patent No.: US 9,028,254 B2
(45) Date of Patent: May 12, 2015

(54) DENTAL PROSTHETICS COMPRISING CURABLE ACRYLATE POLYMER COMPOSITIONS AND METHODS OF THEIR USE

(71) Applicant: Scientific Pharmaceuticals, Inc, Pomona, CA (US)

(72) Inventors: Jan A Orlowski, Altadena, CA (US); David V Butler, West Covina, CA (US); Alice Chin, Monterey Park, CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 0 days.

(21) Appl. No.: 13/941,370

(22) Filed: Jul. 12, 2013

(65) Prior Publication Data

US 2013/0302513 A1    Nov. 14, 2013

Related U.S. Application Data

(60) Continuation of application No. 12/476,918, filed on Jun. 2, 2009, now abandoned, which is a division of application No. 10/914,972, filed on Aug. 10, 2004, now abandoned.

(51) Int. Cl.
| | |
|---|---|
| *A61C 5/00* | (2006.01) |
| *A61K 6/083* | (2006.01) |
| *A61L 24/06* | (2006.01) |
| *A61K 6/00* | (2006.01) |
| *A61K 6/09* | (2006.01) |
| *A61C 13/15* | (2006.01) |
| *A61L 24/04* | (2006.01) |

(52) U.S. Cl.
CPC .............. *A61K 6/083* (2013.01); *A61K 6/0017* (2013.01); *A61K 6/0023* (2013.01); *A61K 6/09* (2013.01); *A61C 19/003* (2013.01); *A61L 24/046* (2013.01)

(58) Field of Classification Search
USPC ..................... 523/117, 116, 118; 433/228.1
See application file for complete search history.

(56) References Cited

U.S. PATENT DOCUMENTS

| | | | |
|---|---|---|---|
| 3,421,766 A | 1/1969 | Chmiel et al. | |
| 3,528,936 A | 9/1970 | Lazzarotto et al. | |
| 3,793,260 A | 2/1974 | Westermann | |
| 3,832,274 A | 8/1974 | Owston | |
| 3,912,685 A | 10/1975 | Gintz | |
| 4,380,432 A | 4/1983 | Orlowski et al. | |
| 5,093,402 A | 3/1992 | Hashimoto et al. | |
| 5,855,632 A | 1/1999 | Stoetzel et al. | |
| 5,969,054 A | 10/1999 | Wamprecht et al. | |
| 6,362,250 B1 * | 3/2002 | Karmaker et al. | 523/116 |
| 6,380,308 B1 | 4/2002 | Wamprecht et al. | |
| 6,509,390 B2 * | 1/2003 | Watanabe et al. | 523/109 |
| 6,630,204 B2 | 10/2003 | Hoelter et al. | |
| 6,709,271 B2 | 3/2004 | Yin et al. | |
| 6,719,995 B2 * | 4/2004 | Rajaiah et al. | 424/435 |
| 6,756,417 B2 | 6/2004 | Allred et al. | |
| 6,899,948 B2 | 5/2005 | Zhang et al. | |
| 6,981,875 B2 * | 1/2006 | Orlowski et al. | 433/220 |
| 7,205,035 B2 * | 4/2007 | Merfeld | 428/34.1 |
| 2002/0002244 A1 | 1/2002 | Hoelter et al. | |
| 2002/0156152 A1 | 10/2002 | Zhang et al. | |
| 2003/0008150 A1 | 1/2003 | Berejka et al. | |
| 2003/0138733 A1 | 7/2003 | Sachdev et al. | |
| 2003/0215588 A1 | 11/2003 | Yeager et al. | |
| 2003/0220460 A1 | 11/2003 | Merfeld | |
| 2007/0197730 A1 | 8/2007 | Li et al. | |

FOREIGN PATENT DOCUMENTS

| | | |
|---|---|---|
| EP | 0 351 838 A2 | 7/1989 |
| JP | 55084307 A | 6/1980 |
| JP | 60-71620 | 4/1985 |
| JP | 09-67223 | 3/1997 |
| JP | 01085209 A | 3/2001 |
| JP | 2001-342231 | 12/2001 |
| JP | 2003192750 | 7/2003 |
| WO | WO 2006/007986 A1 | 1/2006 |

OTHER PUBLICATIONS

U.S. Appl. No. 60/525,173, filed Nov. 26, 2003, Ceska et. al.

* cited by examiner

*Primary Examiner* — Tae H Yoon

(74) *Attorney, Agent, or Firm* — Knobbe Martens Olson & Bear LLP

(57) ABSTRACT

Disclosed herein are acrylic and methacrylic acid ester-based polymeric materials containing as flexibilizing and brittleness reducing agents 1-60% of $C_4$-$C_8$ polyalkylene or polyalkyldiene compounds, preferably having a molecular weight of 300-2100, and the use of such materials in dentistry and medicine.

9 Claims, No Drawings

DENTAL PROSTHETICS COMPRISING CURABLE ACRYLATE POLYMER COMPOSITIONS AND METHODS OF THEIR USE

RELATED APPLICATION INFORMATION

This application is a continuation of U.S. patent application Ser. No. 12/476,918, filed Jun. 2, 2009, now abandoned, which is a divisional of U.S. patent application Ser. No. 10/914,972, filed Aug. 10, 2004, now abandoned.

BACKGROUND OF THE INVENTION

1. Field of the Invention

This invention relates to modified, acrylate polymer compositions featuring reduced brittleness, such polymers being particularly suitable as dental/medical cements and restorative materials and for manufacturing dental prosthetics.

2. Description of the Related Art

Polymeric materials based on the esters of methacrylic acid have found widespread industrial and medical applications. Their role is particularly prominent in dentistry where they have become a base for modern restorative materials, cements, varnishes, cavity liners and sealers. In medicine perhaps the most important uses of acrylic resins include contact lenses and cements used for hip restorations.

Many of these applications require the material to meet a combination of requirements with respect to their chemical, optical and mechanical properties and, frequently, biological compatibility. While acrylic resins, due to a variety of available monomers, usually make it possible to compound a blend which, upon cure, will result in a polymer meeting the requirements of tissue biocompatibility, wear resistance, translucency, mechanical strength or hardness, they frequently fail or are less than satisfactory in applications requiring flexibility. It is especially true in situations where thin layers of polymers are exposed to flexural forces; for example, while placing or removing a well-fitted device. Another example of situations where the greater flexibility and impact resistance of acrylic polymers would be highly desirable are applications where the devices made of such polymeric materials are exposed to rapid or repetitiously applied forces. Especially vulnerable are thin areas of such objects.

In applications requiring longevity, mechanical strength and resistance to exposure to environments which may have a deteriorating effect on the polymeric material by means of wear, chemical reaction, exposure to heat, light, etc., cross-linked acrylic polymers are generally preferred over the linear ones. Consequently, in addition to monounsaturated monomers frequently used in such applications, exemplified by alkylmethacrylates, tetrahydrofurfuryl methacrylate and hydroxyalkyl methacrylates, di-, tri- or even higher polymethacrylates are employed. Such polyfunctional monomers may be used in blends with monofunctionals serving as cross-linking agents, or in compositions where monofunctional monomers are absent. In applications requiring high mechanical strength and chemical and wear resistance, in addition to low polymerization shrinkage and low exotherm of the curing process, higher molecular weight dimethacrylates are generally the monomers of choice. Such monomers are particularly useful in formulating modern self- and light-cured dental restorative materials, prostheses, cements, cavity liners, varnishes and sealers. Their use is also expanding in orthopedic surgery, where they are replacing, or being used as adjuncts to, monomethacrylate monomers to enhance mechanical properties and chemical resistance of resulting polymers.

Acrylic resins have unique features making them difficult to replace with other types of monomers, especially in particular or very demanding applications. These include ease of control of working and curing times, good biocompatibility, and a broad selection of available monomers, and relative ease of synthesizing new ones, having desirable molecular structures allows for modifying or controlling relevant characteristics of cured polymers such as water absorption, solubility, hydrophobicity, adhesive properties, compatibility with various additives, optical properties, mechanical strength, chemical resistance and resistance to heat and UV light. These properties allow for multiple ways of inducing polymerization, such as by chemical means, heat, or light.

These advantages make acrylic resin unique, important and often irreplaceable in many applications, especially in a dental field that has been revolutionized by their advent and consequent expansion.

SUMMARY OF THE INVENTION

Compositions according to preferred embodiments, in which olefinic polymers are used as additives to acrylic polymers, provide more flexible and impact-resistant acrylate polymers suitable for a variety of uses, particularly those related to medical and dental fields. Preferred compositions also effectively address the reducing or eliminating of the oxygen-inhibited layer and/or reducing the exothermic effect of the polymerization process.

Another advantage of polymers in accordance with preferred embodiments, particularly important in medical and dental applications, is their general lack of toxicity as well as a low incidence or absence of allergenic reaction and tissue irritation.

In accordance with preferred embodiments, there is provided a curable composition comprising about 10-90% by weight of one or more acrylic monomers; and about 1-60% by weight of an olefinic component comprising oligomers or polymers of one or more straight chain or branched C4-C6 monomers having one or two double bonds per monomer molecule. The compositions may further comprise one or more additives selected from the group consisting of polymerization initiators, polymerization activators, stabilizers, UV light absorbers, colorants, fillers, therapeutic agents, flavoring agents and viscosity/rheological modifiers. The compositions may exist as one part or component, or they may be in two parts that are mixed together prior to use. The composition may be used in medical and/or dental applications as a medical device such as a restorative material, prosthesis, cement, cavity liner, varnish or sealer.

In accordance with one embodiment, there is provided a method of performing a dental procedure, comprising obtaining a curable composition comprising 10-90% by weight of one or more acrylic monomers and 1-60% by weight of an olefinic component comprising oligomers or polymers of one or more straight chain or branched C4-C6 monomers having one or two double bonds per monomer molecule; applying the composition to at least one surface of a tooth or dental appliance; and allowing the composition to cure.

DETAILED DESCRIPTION OF THE PREFERRED EMBODIMENT

The technology disclosed herein relates to heat, chemically (i.e. self-curable) or light (UV and/or visible) curable acrylate acrylic resin-based formulations as well as polymers or objects resulting from curing of such formulations.

Although acrylic resins have the numerous possible advantages noted above, certain intrinsic characteristics of acrylic resins have limited their scope of application or have complicated their handling or reliability. Such characteristics include brittleness of cured polymers, oxygen-inhibited thin liquid layer remaining on the surface of the cured polymer that leaves a dull surface after being wiped off, and high exothermicity accompanying the polymerization process. Although the high exothermicity is observed primarily during rapid polymerization of unfilled or low-filled lower molecular weight acrylate monomers, such compositions and requirements of fast cure are considered highly desirable in certain clinical applications. Examples of applications raising concern with regard to exothermic effects generated during cure of acrylic monomers include cured or cemented in situ medical and dental devices such as hip prostheses, dental fissure sealers, temporary or permanent crowns and bridges and cemented orthodontic appliances.

There were several prior attempts to address the problems related to the shortcomings of acrylic resins. One such attempt was to use high molecular weight monomethacrylate monomers. While this approach effectively lowered the exothermic effect of the curing process, the resulting polymer was mechanically weak, brittle and the oxygen-inhibited layer was pronounced. A second attempt was to use polyethylene glycols and/or polymeric particulate fillers as inert, nonreactive ingredients. Although polymerization occurred with no excessive heat, the cured material was brittle and cracked easily, even when exposed to weak forces. Oxygen-inhibited layer was, however, slightly reduced. A third attempt was to use inorganic particulate fillers, however, the cured material was brittle and very hard; although the exothermic effect of polymerization and oxygen-inhibited layer were significantly reduced. Another attempt was to add phthalic acid esters and other polymers flexibilizing additives. It was found that such additives, although efficient when incorporated in other type polymers, were of little use in acrylic resin. In addition, concerns were raised about their safety when employed in dental/medical materials.

Disclosed herein are modified, chemically-, heat- or light-curable acrylate compositions and objects made of such compositions. One of the principal features of such compositions, in preferred embodiments, is their temporary or permanent flexibility. (The term "temporary flexibility" is herein defined as transient flexural characteristics of the material during a defined time, usually 1-5 minutes after initial cure.) Such materials also generally exhibit significant improvement over unmodified acrylic polymers in their resistance to breaking under stress. In addition, the oxygen-inhibited layer after polymerization is virtually or entirely eliminated and, if desired, so is the exothermic effect generated during the curing process of the formulations of this invention.

In preferred embodiments, the compositions and objects made of such compositions comprise:

10-90% by weight of one or more esters of acrylic or methacrylic acid containing one or more acrylate or methacrylate moieties per molecule.

1-60% by weight of one or more polymers or oligomers of olefinic monomers having four to six carbon atoms and one or two double bonds per molecule, such polymers preferably having molecular weight of 300-2500 and viscosity of 25-4500 cp.

In the present specification and claims, ranges for components such as those above mean that if there is one recited component, it is present at a concentration within the stated range (as compared to the weight of the entire composition) and if there are two or more species of the recited component present, the total combined weight of all such species will fall within the stated range. Within the range is to be read as inclusive of the upper and lower limits.

The composition optionally comprises one or more of one or more of the following compounds and/or materials: polymerization activating agents, UV absorbers, stabilizers for preventing premature polymerization, organic and/or inorganic fillers, colorants, such as pigments and/or dyes (for aesthetic, diagnostic or use-facilitating purposes), and other desirable additives to enhance mechanical or visual/optical properties of the material. Polymerization activators include, but are not limited to, amines, preferably tertiary amines, and/or peroxides. Preferred polymerization activators include, but are not limited to, benzoyl peroxide, halogen substituted derivatives of benzoyl peroxide, N,N bis-(2-hydroxyethyl) p-toluidine, N,N diethyl-p-toluidine, camphoroquinone, tertiary aliphatic amines, trialkylamines, methacroylalkyl-dialkylamines, and combinations of the foregoing. If present, the one or more polymerization activators are preferably present at concentrations of about 0.5-2% by weight. Stabilizers include, but are not limited to BHT, and, if stabilizers are present, they are preferably present at about 0.01-0.1% by weight, or in sufficient quantity to prevent premature polymerization of the material during storage and/or transport. Preferred fillers include glass, silica (amorphous and/or fumed), quartz silica, aluminum oxide, zirconium oxide, barium sulfate, and mixtures thereof. If present, fillers preferably comprise about 10%-30% of the composition by weight, including about 15%-25%.

The composition may be produced and stored as a single part or it may be as two or more parts, each of which has some or all of the component chemicals and materials of the composition. The two (or more) parts are mixed prior to application or use. Two or more part formulations are preferred for those formulations of the composition which self-cure or chemically cure. For those compositions having two or more parts, the constitution of the composition and the amounts of the component parts refer to the composition following mixing, i.e. the composition as it is used. Accordingly, the individual parts may comprise varying amounts of materials and may be mixed in any proportion such as from 1:20 (v/v) to 20:1 (v/v), provided that the final composition is according to the description herein. In a preferred embodiment, the two parts (Part A and Part B) are mixed in a 1:1 (v/v) ratio by hand or static mixer.

It was unexpectedly found that the addition of such olefinic polymers to acrylic monomers results, after curing of such blends, in a polymeric material having desirable flexural and other mechanical properties, including resistance to impact and breakage. These characteristics made them particularly useful in dental and medical applications. The presence of such olefinic monomers did not interfere with the curing process of the acrylic monomers regardless of whether the curing was done by heat, by chemical means or by light. In addition to desirable mechanical properties of the cured acrylate monomers modified which such olefinic polymers, the surfaces of the resulting product are free, or virtually free, of the oxygen-inhibited layer. Furthermore, the exothermic effect (high exothermicity) of polymerization is virtually not detectable or insignificant.

The discovery of the present compositions came as a total surprise, as polyolefins were known only as modifiers of thermoplastic polymers and elastomers, and not for thermosetting polymers, to which category acrylate polymers belong. Furthermore, it was surprising to find that such olefinic polymers are compatible with a large variety of acrylate monomers and/or their blends, and are useful in a broad range of their molecular weights.

Blends comprising olefinic polymers or oligomers, preferably liquid polymers having molecular weights in the range of approximately 100-700, and aliphatic or aromatic acrylate monomers were found to be particularly advantageous in certain aspects. In some applications, methacrylic acid esters are preferred over acrylic acid ones.

The acrylate component of preferred compositions preferably comprises about 10-90% by weight of an acrylic monomer or a blend of acrylic monomers, including about 50-80%, about 60-80%, about 50-70%, about 60-80%, about 70-80%, and about 50-60% by weight. As used herein, a composition comprising a monomer may be purely monomers, or it may contain some or all of dimers, trimers or other oligomers. The acryate component comprises esters of acrylic or methacrylic acid containing one or more acrylate or methacrylate moieties per molecule. Examples of acrylate monomers suitable for use in formulations of this invention include, but are not limited to: ethylene and propylene glycol dimethacrylates, di-, tri- and polyethylene and propylene glycol dimethacrylates (including, but not limited to, di-polyethylene glycol dimethacrylate, tri-polyethylene glycol dimethacrylate, di-propylene glycol dimethacrylate, and tri-propylene glycol dimethacrylate), tri-methylolopropane trimethacrylate, hydroxyethyl methacrylate, hydroxypropyl methacrylate, tetrahydrofurfuryl methacrylate, 1,6-hexanediol dimethacrylate 7,7,9-trimethyl-4,13-dioxo-3,14-dioxa-5,12-diazahexadecane-1,16-diol dimethacrylate (commonly known as diurethane dimethacrylate), 2,2-bis[4-(2-hydroxy-3-methacryloylpropoxy)phenyl]propane (commonly known as bis-GMA) and ethoxylated bisphenol-A-dimethacrylate (commonly known as EBA). In certain applications, the use of the following aliphatic monomethacrylate monomers, preferably in mixtures with di- or poly-dimethacrylates is desirable: $C_1$-$C_{12}$ alkyl methacrylates, cyclohexyl methacrylate, hydroxy-($C_2$-$C_4$) alkyl methacrylates and glycerol methacrylates.

The olefinic component of preferred compositions preferably comprise about 1-60% by weight of polymers or oligomers of olefinic monomers having four to six carbon atoms, including about 1-10%, about 1-20%, about 10-20%, about 10-30%, about 1-40%, and about 10-40% by weight. Examples of suitable olefinic polymers or oligomers include various olefinic polymers or oligomers derived from $C_4$-$C_6$ mono- or bi-unsaturated monomers, preferably those originated or derived from monomers having four carbon atoms in their lineal chain such as butene, butadiene or methyl butadiene (isoprene). In most applications polybutene is preferred, being inexpensive and commercially available in a desirable range of molecular weights.

The compositions disclosed herein may be formed or molded into medical devices or used as a cement in a medical application, such as a bone cement in orthopedic surgical procedures. The materials may also be molded or formed to create a prosthesis or dental restorative, or it may be applied to a tooth and/or a dental appliance (including but not limited to crowns, bridges, whether permanent or temporary), thereby being used as a cement, cavity liner, varnish, sealer, veneer or a "bonding" material to fill in dental imperfections or a missing portion of a tooth. In accordance with one embodiment, there is provided a method of performing a dental procedure, comprising obtaining a curable composition as disclosed herein in various embodiments; applying the composition to at least one surface of a tooth or dental appliance; and allowing the composition to cure. Accordingly, this disclosure also includes the use of a curable composition as disclosed herein as a cement, cavity liner, varnish, sealer, veneer, bonding material, prosthesis or dental restorative in the treatment of a diseased tooth (such as a tooth having a cavity or decay (caries)), broken tooth, or discolored tooth.

The following examples are given for better understanding of the character of this invention and ways of its implementation; however, with no intention of outlining its scope, defined in the claims.

Example 1

A heat curable composition consisted of:

|  | % (by weight) |
|---|---|
| Diurethane dimethacrylate | 73.58 |
| Polybutene | 9.68 |
| BHT | 0.05 |
| Benzoyl peroxide | 1.06 |
| Silica | 15.63 |

The components were mixed and the material composition was cured in the oven at 100° C. for 1 hour. The properties of cured material are: Barcol hardness: 25-30; Flexural strength: 71 Mpa. The product was judged suitable for intended use, such as for a temporary crown and bridge material.

Example 2

A light curable composition consisted of:

|  | % (by weight) |
|---|---|
| Diurethane dimethacrylate | 73.75 |
| Polybutene | 8.38 |
| Camphoroquinone | 0.26 |
| Methacroyl ethyl diethylamine | 0.75 |
| Silica | 16.86 |

The material was mixed and then cured for 20 seconds using an Optilux® dental curing device (light curing). The product was judged suitable for intended use.

Example 3

A chemically curable composition consisted of a 1:1 (v/v) mixture of Parts A and B:

| Part A | % (by weight) |
|---|---|
| Diurethane dimethacrylate | 78.96 |
| N,N bis(2-hydroxyethyl)-p-toluidine | 0.39 |
| Silica | 20.65 |

| Part B | % (by weight) |
|---|---|
| Diurethane dimethacrylate | 73.58 |
| Polybutene | 9.68 |
| BHT | 0.05 |
| Benzoyl peroxide | 1.06 |
| Silica | 15.63 |

The material was soft cured in 110 seconds and hard cured in 150 seconds at 23° C. (soft cure is defined as a stage at which the material becomes solid but exhibits flexibility). The properties of cured material are: Barcol hardness: 42-45; Flexural strength: 61 Mpa. The product was judged suitable for use.

Example 4

A self curable composition consisted of a 1:1 (v/v) mixture of Parts A and B:

| Part A | % (by weight) |
|---|---|
| EBA | 17.29 |
| Triethylene glycol dimethacrylate | 20.47 |
| Bis-GMA | 14.09 |
| Polybutene | 30.18 |
| BHT | 0.01 |
| N,N bis(2-hydroxyethyl)-p-toluidine | 1.87 |
| Silica | 16.09 |

| Part B | % (by weight) |
|---|---|
| EBA | 18.61 |
| Triethylene glycol dimethacrylate | 21.7 |
| Bis-GMA | 14.88 |
| Polybutene | 16.28 |
| BHT | 0.08 |
| Benzoyl peroxide | 0.77 |
| Silica | 27.68 |

The material reached soft curing stage in 175 seconds and hard cured in 210 seconds at 23° C. The product was judged suitable for use, but was somewhat inferior to the product of Example 3.

Example 5

An alternative self curable composition similar to that of Example 3 but with different filler, consisted of a 1:1 (v/v) mixture of Parts A and B:

| Part A | % (by weight) |
|---|---|
| Diurethane dimethacrylate | 53.92 |
| N,N bis(2-hydroxyethyl)-p-toluidine | 0.38 |
| Silica | 12.97 |
| Glass powder | 32.73 |

| Part B | % (by weight) |
|---|---|
| Diurethane dimethacrylate | 73.58 |
| Polybutene | 9.68 |
| BHT | 0.05 |
| Benzoyl peroxide | 1.06 |
| Silica | 15.63 |

The cured material had similar properties to that of Example 3.

Example 6

A chemically curable composition similar to that of Example 3, but with different flexibilizing additive (polybutadiene instead of polybutene), consisted of a 1:1 (v/v) mixture of Parts A and B:

| Part A | % (by weight) |
|---|---|
| Diurethane dimethacrylate | 79.09 |
| N,N bis(2-hydroxyethyl)-p-toluidine | 0.56 |
| Silica | 20.35 |

| Part B | % (by weight) |
|---|---|
| Diurethane dimethacrylate | 67.03 |
| Polybutadiene | 12.21 |
| BHT | 0.08 |
| Benzoyl peroxide | 1.00 |
| Silica | 19.68 |

The material reached soft curing stage in 85 seconds and hard cured in 140 seconds at 23° C. The product was judged suitable for use.

Example 7

Reference

A chemically curable composition similar to that of Example 3 but not containing flexibilizing additive (polybutene), consisted of a 1:1 (v/v) mixture of Parts A and B:

| Part A | % (by weight) |
|---|---|
| Diurethane dimethacrylate | 72.77 |
| N,N bis(2-hydroxyethyl)-p-toluidine | 0.51 |
| Silica | 26.72 |

| Part B | % (by weight) |
|---|---|
| Diurethane dimethacrylate | 76.33 |
| BHT | 0.05 |
| Benzoyl peroxide | 1.15 |
| Silica | 22.47 |

The properties of cured material are: Barcol hardness: 50-55; Flexural strength: 83 Mpa. The cured product was judged not suitable as a temporary crown and bridge material because of lack of flexibility.

What is claimed is:

1. A method of performing a dental procedure, comprising
    obtaining a curable composition comprising:
        10-90% by weight of one or more acrylic monomers;
        1-60% by weight of polybutene; and
        at least one polymerization activator;
    applying the composition to at least one surface of a tooth or dental appliance; and
    allowing the composition to cure, wherein the allowing the composition to cure comprises applying heat to the composition.

2. A method of performing a dental procedure, comprising
    obtaining a curable composition comprising:
        10-90% by weight of one or more acrylic monomers;
        1-60% by weight of polybutene; and
        at least one polymerization activator;
    applying the composition to at least one surface of a tooth or dental appliance; and
    allowing the composition to cure, wherein the allowing the composition to cure comprises applying UV or visible light to the composition.

3. The method of claim 1 wherein the one or more acrylic monomers are esters of acrylic or methacrylic acid having one to three acrylate or methacrylate groups per molecule.

4. The method of claim 1, wherein the one or more acrylic monomers are selected from the group consisting of ($C_1$-$C_4$) alkylene glycol dimethacrylate, diurethane dimethacrylate, ethoxylated bis-phenol-A dimethacrylate, 2,2-bis[4-(2-hydroxy-3-methacryloylpropoxy)phenyl]propane, hydroxyethyl methacrylate, hydroxypropyl methacrylate, hydroxybutyl methacrylate, and tetrahydrofurfuryl methacrylate.

5. The method of claim 2 wherein the one or more acrylic monomers are esters of acrylic or methacrylic acid having one to three acrylate or methacrylate groups per molecule.

6. The method of claim 2, wherein the one or more acrylic monomers are selected from the group consisting of ($C_1$-$C_4$) alkylene glycol dimethacrylate, diurethane dimethacrylate, ethoxylated bis-phenol-A dimethacrylate, 2,2-bis[4-(2-hydroxy-3-methacryloylpropoxy)phenyl]propane, hydroxyethyl methacrylate, hydroxypropyl methacrylate, hydroxybutyl methacrylate, and tetrahydrofurfuryl methacrylate.

7. The method of claim 1 wherein the polymerization activator comprises benzoyl peroxide or its halogen substituted derivatives.

8. The method of claim 2, wherein the polymerization activator comprises camphoroquinone and/or a tertiary aliphatic amine.

9. The method of claim 8, wherein the tertiary aliphatic amine is selected from the group consisting of trialkylamines, methacroylalkyl-dialkylamines, and combinations thereof.

\* \* \* \* \*